United States Patent [19]

Liddell

[11] 3,948,802

[45] Apr. 6, 1976

[54] COMPOSITION AND METHOD FOR MAINTAINING A CONSTANT CONCENTRATION OF AGENTS AND AMOUNT OF SOLVENT IN A WOOD TREATING PROCESS

[75] Inventor: Harold G. Liddell, Angleton, Tex.

[73] Assignee: The Dow Chemical Company, Midland, Mich.

[22] Filed: Oct. 15, 1974

[21] Appl. No.: 514,688

Related U.S. Application Data

[62] Division of Ser. No. 276,682, July 31, 1972, Pat. No. 3,874,908.

[52] U.S. Cl. .................... 252/404; 21/7; 252/397
[51] Int. Cl.² C09K 15/08; B27K 3/00; C09K 15/00
[58] Field of Search ................ 252/404, 397; 21/7; 117/147, 59, 57

[56] References Cited
UNITED STATES PATENTS

| | | | |
|---|---|---|---|
| 3,039,843 | 6/1962 | Chamberlain | 21/7 |
| 3,351,485 | 11/1967 | Langner | 117/147 |
| 3,541,171 | 11/1970 | Starnes | 252/404 |
| 3,634,289 | 11/1972 | Liddell | 252/404 |
| 3,685,959 | 9/1972 | Dunn | 21/7 |
| 3,702,784 | 11/1972 | Farquhar | 21/7 |
| 3,756,960 | 9/1973 | Junghahnel | 252/404 |
| 3,785,770 | 1/1974 | Hudson | 117/147 |

Primary Examiner—Richard D. Lovering
Assistant Examiner—Donald P. Walsh
Attorney, Agent, or Firm—Glwynn R. Baker

[57] ABSTRACT

In a wood treating process wherein wood is impregnated with a halogenated solvent solution containing a wood preservative and an antiblooming additive and excess solvent is vaporized from the impregnated wood and condensed for return to the used impregnation solution, the depleted solution is restored to its original composition for recycle to the process by addition of a concentrate of the preservative and antiblooming additive in the solvent. Preferred components of the treating solution and the concentrate are pentachlorophenol, a glycol or glycol derivative, and a relatively low boiling chlorinated solvent such as methylene chloride.

4 Claims, No Drawings

COMPOSITION AND METHOD FOR MAINTAINING A CONSTANT CONCENTRATION OF AGENTS AND AMOUNT OF SOLVENT IN A WOOD TREATING PROCESS

CROSS-REFERENCE TO RELATED APPLICATION

This is a division, of application Ser. No. 276,682 filed July 31, 1972, now U.S. Pat. No. 3,874,908.

BACKGROUND OF THE INVENTION

The utilization of halogenated hydrocarbon solvents as carriers for the impregnation of wood with preservatives, dyes, antiblooming agents, fire-retardants and the like has provided the art with a process superior to creosote oil, petroleum oil or liquefied petroleum gas techniques. The halogenated hydrocarbon solvent process is less expensive and more versatile, providing treated wood which is lighter, and therefore generally less expensive to ship. Also, wood treated in this manner has good retention of the additives and may be painted which was more difficult or impossible with older techniques. Such halogenated solvent processes generally comprise soaking wood in a solution of a wood preservative in a relatively low boiling solvent such as methylene chloride or trichloroethylene. Pentachlorophenol is a commonly used preservative. The solution may also contain an antiblooming additive such as a glycol or glycol derivative. The soaking step may be carried out at ambient or somewhat elevated temperature and pressure. When the wood has been sufficiently impregnated by the treating solution, the excess solution is drawn off and the wood is heated to vaporize the solvent in the wood. Solvent removal is completed by air drying. A final treatment of the wood by application of reduced pressure may also be used for this purpose.

The wood treating technique using a halogenated hydrocarbon solvent results in a loss of from about one-half to one and one-half pounds of solvent per cubic foot of wood treated in addition to the additives retained by the wood. Thus, it has been necessary for the operator to "test and add" to his treating tank in order to maintain the desired concentration of treating agents and to make-up solvent lost. In the test and add technique, since many of the preservatives are not readily soluble in the halohydrocarbon solvent and preservatives such as pentachlorophenol are soluble only to about 10 percent by weight in the solvent, the operator must recirculate large quantities of solvent through a solid bed of the preservative to his storage tank. The present invention provides a composition and method for replenishing the depleted treating solution by the continuous or intermittent addition of the liquid concentrate, thereby maintaining the concentration of the treating agents and replacing lost solvent at the same time.

SUMMARY OF THE INVENTION

It has been found that lost solvent and depleted preservative and antiblooming additive are conveniently and simultaneously replaced in a wood treating process as described above by adding to the used treating solution a concentrate which is a homogeneous solution or dispersion in a halogenated hydrocarbon solvent of about 5 to about 40 weight percent of a wood preservative and about 2 to about 60 percent of an antiblooming additive which is at least one of ethylene glycol, propylene glycol, a corresponding liquid polygycol of molecular weight up to about 4000, or a lower alkyl monoether of such a glycol or polyglycol. Halogenated aliphatic hydrocarbon solvents of 1–3 carbon atoms and a boiling point from ambient temperature up to about 140°C. are suitable. Other wood treating additives such as dyes may also be present in the concentrate in minor amounts, but those listed are the essential components.

DETAILED DESCRIPTION

The use of the polyglycol or the glycol ether allows a larger amount of preservative to be held in the concentrate as well as providing beneficial characteristics to the treated wood. Thus, it acts as a co-solvent in the threecomponent system and it also aids the retention of the preservative in the wood. Only about 9% by weight of pentachlorophenol is soluble in methylene chloride alone, whereas if the concentrate solution contains about 20–25% by weight of glycol, polyglycol or glycol ether, as much as about 40% by weight of the preservative can be present in solution, the remainder being the methylene chloride. Similarly, chloroform, ethylene dichloride, methyl chloroform, trichloroethylene, dichloroethylene, perchloroethylene and the like have relatively low solvency for most wood preservative agents, especially the chlorinated phenols. With these solvents, the use of a glycol, polyglycol or glycol ether as a co-solvent also makes it possible to dissolve a substantially larger amount of preservative in the concentrate solution.

In order to more clearly understand the novelty and usefulness of the present invention, a typical solvent wood treating process is hereafter described.

Wood impregnation with a preservative is achieved by soaking wood under pressure in a solution of the desired preservative in a halogenated hydrocarbon solvent with glycol additive and subsequently steaming or otherwise heating the treated wood to recover the solvent employed to carry the preservative into the wood. A finishing application of reduced pressure to the heated wood may be employed to remove more residual solvent and water. Wood treated in this manner contains little or no residual solvent, as compared to the previous techniques, and is therefore essentially free of surface bleeding. The process likewise provides the additional advantage of producing a treated wood product which retains the light color and natural appearance of untreated wood and which does not darken with age.

The present invention is preferably used as an added step in a wood treating process comprising the following operations:

1. Wood in the desired form such as poles, lumber, timbers, or the like is contacted in a suitable treating chamber with a solution or dispersion in a halogenated hydrocarbon solvent, preferably methylene chloride, containing about 2–6 percent by weight of a wood preservative such as pentachlorophenol and about 0.5–4 percent of a glycol or glycol ether antiblooming agent at ambient temperature to about 140°C. and at a pressure at least sufficient to maintain the solvent in the liquid state at 10operating temperature. The time of contact may be from 1 to 12 hours, depending upon the type and species of wood employed.

2. The excess solution is removed from contact with the wood and returned to storage.

3. The treated wood is heated at least to the boiling point of the solvent, preferably with steam, and the solvent vapors thereby formed are condensed and combined in storage with the excess solution removed in step (2), thereby forming a wood treating solution containing lower concentrations of both preservative and antiblooming agent that the original solution.

4. (Optional) The heated wood is subjected to reduced pressure to vaproize most of the residual solvent in the wood and the solvent vapors are condensed and combined with the recovered solution and solvent from steps (2) and (3).

The concentrate of the present invention is then added as the sole source of makeup to the depleted wood treating solution in a quantity sufficient to restore it to its original concentrations of preservative and antiblooming agent and the restored solution is returned to the process for another wood treating cycle. In the above-described process, some modifications of procedure or materials may be made without altering the essential nature of the process. For example, in step (3), the wood can be heated with superheated solvent vapors rather than steam, thereby reducing the volume of water which has to be separated from the condensed vapors before returning the recovered solvent to storage.

A preferred concentrate composition consists essentially of about 10 – 35 percent by weight of pentachlorophenol and about 5 – 55 percent of glycol antiblooming additive in methylene chloride. Although any of the glycols and glycol ethers described below can be used to advantage in the process, particularly preferred antiblooming additives are diethylene glycol and polypropylene glycol of about 750 molecular weight.

The treated wood produced by this process as described above has a clean, natural appearance when removed from the treating chamber and is essentially ready for use at that time.

The amounts of preservative and the depth of penetration necessary to provide the desired protection are well known to those skilled in the art of wood preservation. In the case of pentachlorophenol and closely related compounds, a desirable concentration is from about 0.35 to 0.7 lbs. of preservative per cubic foot of wood on a dry weight basis, depending upon the species of wood.

Halogenated aliphatic hydrocarbon solvents suitable for use in the present invention are those which have boiling points of from about room temperature up to about 140°C., preferably up to about 100°C. Examples of such solvents are the polyhalomethanes, polyhaloethanes and polyhaloethylenes such as methylene chloride ($CH_2Cl_2$), chloroform ($CHCl_3$), carbon tetrachloride ($CCl_4$), methylene chlorobromide ($CH_2ClBr$), 1,1,1-trichloroethane ($Cl_3CCH_3$), dibromodifluoroethane (BrFCHCHFBr) trichlorotrifluoroethane ($Cl_2FC.CF_2Cl$), tetrafluorodibromoethane ($BrF_2C.CF_2Br$), tetrachlorodifluoroethane ($Cl_2FC.CFCl_2$), cis- and trans-dichloroethylene (ClCH:CHCl), trichloroethylene ($Cl_2C$:CHCl), perchloroethylene ($Cl_2C$:$CCl_2$), 1,1-dichloroethane ($Cl_2CHCH_3$), ethylene dichloride ($CH_2ClCH_2Cl$), 1,1,2-trichloroethane ($ClCH_2CHCl_2$) and the like. Particularly preferred solvents are lower boiling chlorinated compounds such as methylene chloride and trichloroethylene.

Wood preserving agents which can be employed in this invention include those which are solvent-soluble or solvent-dispersible, unreactive with the solvent and are essentially nonvolatile at or below the boiling point of the solvent from which they are being impregnated into the wood. If more than one such agent is utilized, it is desirable that they do not react with one another in such a way as to interfere with the property or properties which they are intended to impart to the wood.

It is preferred that the agents be soluble in the solvent selected, but the solubility need not be great. For example, as little solubility as about one weight percent of preservative is operable, but generally, preservatives are used which are soluble at least to the extent of about 2 to 6 weight percent. Polyglycol and glycol ether antiblooming agents are employed in from about 0.5 to about 4 weight percent based upon the weight of solvent and these of course increase the amount of polychlorinated phenols and other preservatives that can be dissolved in the composition.

Wood preservatives for use in the process described above and which are employed in preparing the concentrates of this invention include pentachlorophenol, 2,3,4,6-tetrachlorophenol, 2,4,5-trichlorophenol, 2,4,6-trichlorophenol, 4-chloro-2-chloropentylphenol, beta-napththol, copper naphthenate and phenyl mercury oleate. Other known wood-preservative compounds which are soluble or can be dispersed in halogenated hydrocarbon solvents with the aid of co-solvents or dispersants may also be used. Pentachlorophenol and its mixtures with tetrachlorophenol are preferred.

Glycols suitable for preparing the concentrate of the present invention on and which are also useful in providing antiblooming properties are ethylene glycol, propylene glycol and corresponding liquid polyalkylene glycols having molecular weights of up to about 4000. Glycol ethers which are useful in accordance with the present invention are those liquid $C_{1-4}$ alkyl monoethers of these glycols and polyglycols such as the methyl, ethyl and butyl monoethers of the mono-, di- and tri-ethylene and propylene glycols. Representatives of the above class of solvents are propylene gylcol, diethylene glycol, dipropylene glycol, tripropylene glycol, ethylene glycol methyl ether, diethylene glycol butyl ether, propylene glycol methyl ether, dipropylene glycol methyl ether, and tripropylene glycol methyl ether. Mixtures of two or more of such compounds can be used.

EXAMPLE 1

A treating solution of pentachlorophenol and diethylene glycol in methylene chloride which had been used in the wood treating process, and which had originally contained about 5.0% penta and 2.5% glycol based on the total weight of solution, was found by analysis after treatment to contain 2.5% penta and 1.25% glycol. To 1000 pounds of this depleted solution was added 110 pounds of concentrate containing 28.6% pentachlorophenol and 14.3% diethylene glycol, the remainder being methylene chloride. The resulting 1110 pounds of solution contained 5.09% pentachlorophenol and 2.54% diethylene glycol, which was then at the proper concentration for processing more wood.

EXAMPLE 2

In another instance a somewhat stronger concentrate was used to replenish the depleted wood treating solution. Thus to a thousand pounds of treating solution was added 70 pounds of a concentrate containing 33.3% penta and 22.2% diethylene glycol in methylene chloride based on the total weight of the concentrate. The treating solution was thus brought from a concentration of 3.0% penta and 1.5% glycol to a useable concentration of 4.98% penta and 2.85% glycol.

We claim:

1. A wood treating composition of matter comprising:
   A. from about 10 to about 40 weight percent of a wood preservative; and
   B. from about 5 to about 60 weight percent of at least one of ethylene glycol, proplylene glycol, a corresponding liquid polyglycol having a molecular weight up to about 4000, or a mono alkyl ether of ethylene or propylene glycol or polyglycol both dissolved or dispersed in a halogenated aliphatic hydrocarbon solvent of 1-2 carbon atoms, said solvent boiling between about ambient tempeerature and 140°C.

2. The composition of claim 1 wherein the wood preservative is pentachlorophenol.

3. The composition of claim 2 wherein the solvent is methylene chloride.

4. The composition of claim 3 wherein the glycol component is diethylene glycol.

* * * * *

UNITED STATES PATENT AND TRADEMARK OFFICE
CERTIFICATE OF CORRECTION

PATENT NO. : 3,948,802
DATED : April 6, 1976
INVENTOR(S) : Harold G. Liddell

It is certified that error appears in the above-identified patent and that said Letters Patent are hereby corrected as shown below:

In the "Abstract", lines 5 and 6, delete "impregnation" and insert -- impregnating --

Col. 1, line 46, put quotation marks -- " -- around -- "test and add" --

Col. 2, line 2, delete "polygycol" and insert -- polyglycol --

Col. 2, line 17, delete "threecomponent" and insert -- three-component --

Col. 2, line 64, delete "10operating" and insert -- the operating --

Col. 3, line 7, delete "that" and insert -- than --

Col. 3, line 56, insert a comma --,-- after "(BrFCHCHFBr)"

Col. 4, line 40, delete "gylcol" and insert -- glycol --

Col. 5, line 11, delete "proplylene" and insert -- propylene --

Col. 6, line 4, delete "tempeera-" and insert -- tempera- --

Signed and Sealed this

Thirty-first Day of August 1976

[SEAL]

Attest:

RUTH C. MASON
Attesting Officer

C. MARSHALL DANN
Commissioner of Patents and Trademarks